US00PP14248P29

(12) United States Plant Patent
Bradford

(10) Patent No.: US PP14,248 P2
(45) Date of Patent: Oct. 21, 2003

(54) NECTARINE TREE NAMED 'EARLY PEARL'

(50) Latin Name: *Prunus persica*
Varietal Denomination: Early Pearl

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/299,083

(22) Filed: Nov. 19, 2002

(51) Int. Cl.[7] ..... A01H 5/00
(52) U.S. Cl. ..... Plt./188
(58) Field of Search ..... Plt./188

(56) References Cited

U.S. PATENT DOCUMENTS

PP9,360 P 11/1995 Bradford

PP10,293 P 3/1998 Bradford

*Primary Examiner*—Bruce R. Campell
*Assistant Examiner*—W C Haas

(57) ABSTRACT

The present invention relates to a nectarine tree, *Prunus persica,* and more particularly to a new and distinct variety broadly characterized by a large size, vigorous, hardy, self-fertile, productive and regular bearing tree. The fruit matures under the ecological conditions described approximately the last week in May, with first picking on May 27, 2002. The fruit is uniformly medium in size, very good in flavor, globose in shape, clingstone in type, moderately firm in texture, white in flesh color, and red in skin color. The variety was developed as a first generation cross using 'July Pearl' (U.S. Plant Pat. No. 10,293) white flesh nectarine as the selected seed parent and an unnamed nectarine as the selected pollen parent.

1 Drawing Sheet

Botanical classification: *Prunus persica.*

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'EARLY PEARL'. The present variety was hybridized by me in 1997, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'July Pearl' (U.S. Plant Pat. No. 10,293) white flesh nectarine as the selected seed parent and an unnamed nectarine as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'July Pearl' (U.S. Plant Pat. No. 10,293) nectarine, by producing nectarines that are globose in shape, fairly firm in texture, mostly red in skin color, and white in flesh color, but is distinguished therefrom and an improvement thereon by producing fruit that matures about six weeks earlier.

The present variety is most similar to 'June Pearl' (U.S. Plant Pat. No. 9,360) nectarine by producing nectarines that are white in flesh color, nearly full red in skin color, and sweet subacid in flavor, but is distinguished therefrom and an improvement thereon by having leaves with globose instead of reniform glands and by producing fruit that matures about sixteen days earlier and is globose instead of oblong in shape.

DRAWING

The accompanying photograph exhibits four whole fruits positioned to display the characteristics of the skin color and form, one fruit divided along the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 1, 2002, on the original tree during its fifth growing season. All major color code designations are by reference to the Inter-Society Color Council, National Bureau of Standards. Common color names are also used occasionally.

TREE

Size: Large, reaching a height of 12' [3.66 m.] and a spread of 8' [2.44 m.] after five growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Trunk:
*Size.*—Medium, with a maximum diameter of 3⅝" [92 mm.] after the fifth growing season.
*Texture.*—Shaggy.
*Bark color.*—Dark grayish yellowish brown [81. d.gy.yBr].
*Lenticels.*—Approximate Number Per Square Inch: 12. Color: Brownish orange [54. brO]. Typical Size: 3/16" to ⅜" [4.8–9.5 mm.].
Branches:
*Size.*—Diameter of limb is 1⅝" [41 mm.] measured 12" above the secondary fork, typical of *Prunus persica,* and dependent upon cultural practices and climatic conditions.
*Texture.*—Smooth on 1st year wood, increasing roughness with age.
*Color.*—1st Year Wood Topside: Grayish red [19. gy.R]. 1st Year Wood Underside: Brilliant yellow green [116. brill.YG]. Older Wood: Deep yellowish brown [75. deep yBr].
*Lenticels.*—Approximate Number Per Square Inch: 60. Color: Light orange yellow [70. l.OY]. Typical size: 1/16" to 3/16" [1.6–4.8 mm.].
Leaves:
*Size.*—Medium. Average Length: 5¼" [133 mm.]. Average width: 1½" [38 mm.].
*Arrangement.*—Alternate.
*Thickness.*—Medium.
*Form.*—Elliptical.
*Apex.*—Acuminate.
*Base.*—Acute, with an average base angle of 110 degrees.
*Surface.*—Smooth.
*Color.*—Dorsal Surface: Dark yellowish green [137. d.yG]. Ventral Surface: Moderate olive green [125. m.OlG].
*Margin.*—Finely serrate.
*Venation.*—Pinnately net veined.
*Petiole.*—Average Length: 7/16" [11.1 mm.]. Average Thickness: 1/16" [1.6 mm.]. Color: Light yellow green [119. l.YG].
*Stipules.*—Number: 2 per leaf, up to 6 per growing tip. Average Length: ¼" [6.4 mm.]. Color: Light yellow green [119. l.YG] when growing.
*Glands.*—Number: 1 to 4, usually 2. Position: Usually alternate, positioned on both the petiole and base of blade. Size: Small. Form: Globose. Color: Light yellow green [119. l.YG] on younger leaves acquiring Dark red [16. d.R] centers with age.
*Leaf buds.*—Conic.
Flower buds:
*Hardiness.*—Hardy, with respect to central California winters.
*Diameter.*—Typically 5/16" [7.9 mm.] 1 week before bloom.
*Length.*—Typically ½" [12.7 mm.] 1 week before bloom.
*Form.*—Not appressed.
*Surface.*—Pubescent.
*Color.*—Moderate purplish red [258. m.pR].
Flowers: Perfect, complete, perigynous, usually a single pistil, typically thirty or more stamens, five sepals and petal locations alternately positioned.
*Type.*—Showy, large.
*Average flower diameter.*—1⅞" [47.6 mm.].
*Number of petals.*—Usually five, with about 20 percent double blossoms.
*Petal shape.*—Circular.
*Petal margin.*—Slightly wavy.
*Average petal diameter.*—11/16" [17.5 mm.].
*Average petal length.*—⅞" [22.2 mm.].
*Petal apex.*—Rounded.
*Petal base.*—Rounded.
*Petal color.*—Pale purplish pink [252. p.pPk].
*Anther color.*—Deep reddish orange [36. deep rO].
*Stigma color.*—Light greenish yellow [101. l.gY].
*Sepal color.*—Grayish purplish red [262. gy.pR].
*Sepal length.*—¼" [6 mm.].
*Sepal width.*—3/16" [5 mm.].
*Average pistil length.*—13/16" [20.6 mm.].
*Average stamen length.*—¾" [19.1 mm.].
*Fragrance.*—Moderate when nectar is present.
*Blooming period.*—Medium compared with other varieties.
*Onset of bloom.*—One percent on Mar. 4, 2002.
*Date of full bloom.*—Mar. 11, 2002.
*Duration of bloom.*—One to two weeks, dependent on ambient temperature.
*Number per cluster.*—1 to 3 with single flowers most common.

FRUIT

Maturity when described: Firm ripe, Jun. 1, 2002.
Date of first picking: May 27, 2002.
Date of last picking: Jun. 7, 2002.
Size: Uniform, medium.
*Average diameter axially.*—2⅝" [66.7 mm.].
*Average diameter across suture plane.*—2⅝" [66.7 mm.].
*Typical weight.*—5.3 ounces [150 grams].
Form: Uniform, symmetrical, globose.
*Longitudinal section form.*—Circular.
*Transverse section through diameter.*—Circular.
Suture: An inconspicuous line near the base becoming a shallow groove toward the apex, and ending with a marked depression just beyond the pistil point.
Ventral surface: Rounded, lipped toward the apex.
Lips: Slightly unequal.
Cavity: Flaring, circular, suture showing on one side, Yellowish white [92. yWhite] stem markings typical.
*Depth.*—½" [12.7 mm.].
*Breadth.*—⅞" [22.2 mm.].
Base: Somewhat truncate.
Apex: Rounded.
Pistil point: Oblique, negligible in length, depressed within the suture.
Stem: Medium.
*Average length.*—5/16" [7.9 mm.].
*Average width.*—3/16" [4.8 mm.].
Skin:
*Thickness.*—Medium.
*Surface.*—Smooth.
*Tenacity.*—Tenacious to flesh.

*Astringency.*—Nonastringent.
*Tendency to crack.*—Slight in wet season.
*Color.*—Very dark red [17. v.d.R] over a Strong red [12. s.R] background with slight Light orange yellow [70. l.OY] freckling toward the apex.

Flesh:
*Color.*—White [263. White] with a slight amount of Moderate red [15. m.R] flecking throughout.
*Surface of pit cavity.*—Yellowish white [92. yWhite] fibers breaking when twisted from the stone.
*Amygdalin.*—Scarce.
*Juice.*—Abundant, rich.
*Texture.*—Moderately firm, crisp.
*Fibers.*—Abundant, fine.
*Ripens.*—Slightly earlier toward the apex.
*Flavor.*—Subacid and sweet, averaging 14 brix.
*Aroma.*—Slight.
*Eating quality.*—Very good.

STONE

Type: Clingstone.
Form: Oval.
Hilum: Narrow.
Base: Straight.
Apex: Acute, with an average tip length of ⅛" [3.2 mm.].
Sides: Equal.
Surface: Irregularly furrowed near the apex and pitted toward the base.
Ridges: Jagged toward the base.
Color: Light yellowish brown [76. l.yBr].
Average pit wall thickness: ¼" [6.4 mm.].
Average width: 1" [25.4 mm.].
Average length: 1⅜" [34.9 mm.].
Average breadth: ¾" [19.1 mm.].
Tendency to split: Slight.
Kernel:
*Form.*—Oval.
*Pellicle color.*—Grayish yellow [90. gy.Y].
*Skin color.*—Pale yellow [89. p.Y] when freshly removed.
*Vein color.*—Brilliant orange yellow [67. brill.OY].
*Taste.*—Very bitter.
*Viable.*—Yes, but only by utilizing embryo rescue techniques.
*Average width.*—½" [12.7 mm.].
*Average length.*—11/16" [17.5 mm.].
*Amygdalin.*—Abundant.

USE

Market: Fresh market and long distance shipping.
Keeping quality: Good. Fruit quality observed to remain in good condition in after 17 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'June Pearl' (U.S. Plant Pat. No. 9,360) nectarine by producing nectarines that are white in flesh color, nearly full red in skin color, and sweet subacid in flavor, but is distinguished therefrom and an improvement thereon by having leaves with globose instead of reniform glands and by producing fruit that matures about sixteen days earlier and is globose instead of oblong in shape.

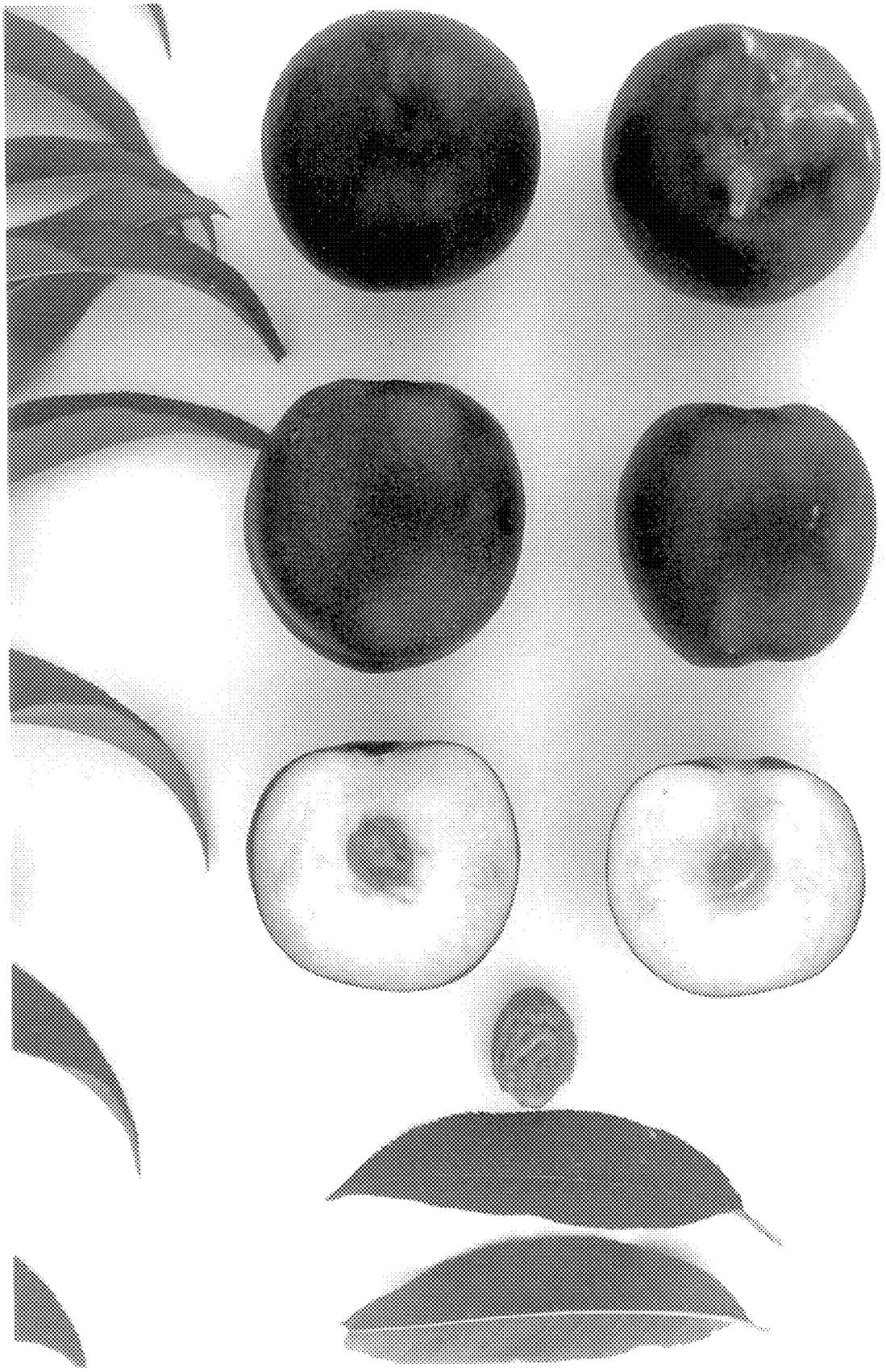

* * * * *